US008551954B2

(12) United States Patent
Schmidtchen et al.

(10) Patent No.: US 8,551,954 B2
(45) Date of Patent: Oct. 8, 2013

(54) ANTIMICROBIAL PEPTIDES WITH HEPARIN BINDING ACTIVITY

(75) Inventors: Artur Schmidtchen, Lund (SE); Martin Malmsten, Täby (SE)

(73) Assignee: Pergamum AB, Solna (SE)

(*) Notice: Subject to any disclaimer, the term of this patent is extended or adjusted under 35 U.S.C. 154(b) by 1361 days.

(21) Appl. No.: 11/877,394

(22) Filed: Oct. 23, 2007

(65) Prior Publication Data

US 2009/0074864 A1 Mar. 19, 2009

Related U.S. Application Data

(62) Division of application No. 10/557,455, filed as application No. PCT/SE2004/000797 on May 19, 2004.

(60) Provisional application No. 60/320,204, filed on May 19, 2003.

(30) Foreign Application Priority Data

May 19, 2003 (SE) ....................................... 0301431

(51) Int. Cl.
*A61K 33/30* (2006.01)
*A61K 33/34* (2006.01)
*A61K 33/06* (2006.01)
*A61K 38/10* (2006.01)
*A61K 38/16* (2006.01)

(52) U.S. Cl.
USPC ........................................... 514/21.4; 514/1.1

(58) Field of Classification Search
None
See application file for complete search history.

(56) References Cited

U.S. PATENT DOCUMENTS

| 6,284,726 B1 | 9/2001 | Colman et al. | |
| 6,699,505 B2 * | 3/2004 | Shastri et al. | 424/486 |
| 7,732,655 B2 * | 6/2010 | Cullen et al. | 602/48 |
| 2004/0058870 A1 * | 3/2004 | Froland et al. | 514/12 |

FOREIGN PATENT DOCUMENTS

| JP | 08208692 | * | 8/1996 |
| WO | WO 94/20532 | | 9/1994 |
| WO | WO 98/58960 | | 12/1998 |
| WO | WO 00/27415 | | 5/2000 |
| WO | WO 00/27866 | | 5/2000 |

OTHER PUBLICATIONS http://dictionary.reference.com/browse/moiety, pp. 1-4. Accessed Aug. 26, 2010.*
JP 08208692 machine translation, pp. 1-12. Accessed Aug. 11, 2011.*
Bacteria from http://users.rcn.com/jkimball.ma.ultranet/BiologyPages/E/Eubacteria.html. pp. 1-9. Accessed Jun. 18, 2009.
Virus from http://www.ucmp.berkely.edu/allife/virus.html. pp. 1-2. Accessed Jun. 18, 2009.
*Enterococcus faecalies* from http://web.mst.edu/-microbio/BIO221_2005/E_faecalis.htm, pp. 1-2 Accessed Jun. 18, 2009.
*Streptococcus pneumoniae* from http://emedicine.medscape.com/article/225811-overview, pp. 1-10. Accessed Jun. 18, 2009.
Herwald H, Dedio J. Kellner R. Loos M, Muller-Esterl W. :Isolation and Characterization of the Kininogen-binding Protein. pp. 33 from Endothelial Cells, JCB, 1996, 271(22): 13040-13047.
Kunapuli SP, DeLa Cadena RA, Colman RW, "Deletion Mutagenesis of High Molecular Weight Kininogen Light Chain," JCB, 1993, 264(4): 2486-2492.
Rudinger J, "Characteristics of the amino acids as components of a peptide hormone sequence," Peptide Hormons, JA Parsons Edition, University Park Press, Jun. 1976, pp. 1-7.
"Designing Custom Peptides," from SIGMA Genosys, pp. 1-2. Accessed Dec. 16, 2004.
Schinzel R, Drueckes P, "The phosphate recognition site of *Escherichia coli* maltodextrin phosphorylase," FEBS, Jul. 1991, 286(1,2): 125-128.
Voet D, Voet JG, Biochemistry, Second Edition, John Wiley & Sons, Inc. 1995, pp. 235-241.
Ngo JT, Marks J, Karplus M, "Computational Complexity, Protein Structure Prediction, and the Levinthal Paradox," The Protein Folding Problem and Tertiary Structure Predition, K. Merc Jr. and S. Le Grand Edition, 1994, pp. 491-495.
Pixley et al. "Fine mapping of the sequences in domain 5 of high molecular weight kininogen (HK) interacting with heparin and zinc." *J. of Thrombosis and Haemostasis.* vol. 1. 2003. pp. 1791-1798.
Bradeley CM, Barrick D, "Limits of Cooperativity in a Structurally Modular Protein: Response of the Notch Ankyrin Domain to Analgous Alanine Substitutions in Each Repeat," J Mol. Biol. 2002. 324:373-386.
Database acc. No. AAY93344, Nov. 28, 2005.
Database Geneseq Patent [Online] Feb. 4, 1997 retrieved from EBI Database accession No. AAW07625. Database Geneseq Patent [Online] Jul. 2, 1997 retrieved from EBI Database accession No. E60742.
Acc. No. A81818, Jan. 21, 2000 retrieved from EBI.
Acc. No. A81813, Jan. 21, 2000.

(Continued)

*Primary Examiner* — Julie Ha
(74) *Attorney, Agent, or Firm* — Merchant & Gould P.C.

(57) ABSTRACT

An antimicrobial peptide with heparin binding activity is described. It can be derived from endogenous mammalian proteins being substantially free from antimicrobial activity selected from the group consisting of laminin isoforms, complement factor C3, histidin rich glycoprotein and kininogen and having from 10 to 36 amino acids residues, wherein the antimicrobial peptide consists of at least four amino acid residues selected from the group consisting of K,R, and H. Also described are pharmaceutical compositions comprising said antimicrobial peptide and use of the antimicrobial peptide and/or antimicrobial/pharmaceutical composition.

19 Claims, 6 Drawing Sheets

(56) References Cited

OTHER PUBLICATIONS

McCabe et al. "Basic Residues in Azurocidin/HBP Contribute to Both Heparin Binding and Antimicrobial Activity." Jul. 26, 2002 *The Journal of Biological Chemistry*. vol. 277, No. 30 pp. 27477-27488.
Margalit et al. "Comparative Analysis of Structurally Defined Heparin Binding Sequences Revels a Distinct Spatial Distribution of Basic Residues." Sep. 15, 1993 *The Journal of Biological Chemistry*. vol. 268, No. 26. pp. 19228-19231.
Lin et al. "Kinetic Analysis of the Role of Zinc in the Interaction of Domain 5 of High-Molecular Weight Kininogen (HK) with Heparin." 2000. *Biochemistry*. vol. 39. pp. 5104-5110.
Andersson et al. "Antimicrobial activities of heparin-binding peptides." 2004. *Eur. J. Biochem.* vol. 271. pp. 1219-1226.

* cited by examiner

SEQUENCE LISTING

```
<160> NUMBER OF SEQ ID NOS: 38

<210> SEQ ID NO 1
<211> LENGTH: 20
<212> TYPE: PRT
<213> ORGANISM: Artificial Sequence
<220> FEATURE:
<223> OTHER INFORMATION: derived from kininogen

<400> SEQUENCE: 1

His Lys His Gly His Gly His Gly Lys His Lys Asn Lys Gly Lys Lys
1               5                   10                  15

Asn Gly Lys His
            20

<210> SEQ ID NO 2
<211> LENGTH: 19
<212> TYPE: PRT
<213> ORGANISM: Artificial Sequence
<220> FEATURE:
<223> OTHER INFORMATION: derived from kininogen
```

```
<400> SEQUENCE: 2

Gly Gly His Val Leu Asp His Lys His Gly His Gly His Lys
1               5                   10                  15

Asn Lys Gly

<210> SEQ ID NO 3
<211> LENGTH: 20
<212> TYPE: PRT
<213> ORGANISM: Artificial Sequence
<220> FEATURE:
<223> OTHER INFORMATION: derived from kininogen

<400> SEQUENCE: 3

Lys His Asn Leu Gly His Gly His Lys His Glu Arg Asp Gln Gly His
1               5                   10                  15

Gly His Gln Arg
            20

<210> SEQ ID NO 4
<211> LENGTH: 20
<212> TYPE: PRT
<213> ORGANISM: Artificial Sequence
<220> FEATURE:
<223> OTHER INFORMATION: derived from histidin-rich glycoprotein

<400> SEQUENCE: 4

Gly His His Pro His Gly His His Pro His Gly His His Pro His Gly
1               5                   10                  15

His His Pro His
            20

<210> SEQ ID NO 5
<211> LENGTH: 26
<212> TYPE: PRT
<213> ORGANISM: Artificial Sequence
<220> FEATURE:
<223> OTHER INFORMATION: derived from complement factor C3

<400> SEQUENCE: 5

Leu Arg Lys Cys Cys Glu Asp Gly Met Arg Glu Asn Pro Met Arg Phe
1               5                   10                  15

Ser Cys Gln Arg Arg Thr Arg Phe Ile Ser
            20                  25

<210> SEQ ID NO 6
<211> LENGTH: 27
<212> TYPE: PRT
<213> ORGANISM: Artificial Sequence
<220> FEATURE:
<223> OTHER INFORMATION: derived from complement factor C3

<400> SEQUENCE: 6

Leu Gly Glu Ala Cys Lys Lys Val Phe Leu Asp Cys Cys Asn Tyr Ile
1               5                   10                  15

Thr Glu Leu Arg Arg Gln His Ala Arg Ala Ser
            20                  25

<210> SEQ ID NO 7
<211> LENGTH: 21
<212> TYPE: PRT
<213> ORGANISM: Artificial Sequence
<220> FEATURE:
<223> OTHER INFORMATION: derived from complement factor C3
```

```
<400> SEQUENCE: 7

Cys Asn Tyr Ile Thr Glu Leu Arg Arg Gln His Ala Arg Ala Ser His
1               5                   10                  15

Leu Gly Leu Ala Arg
            20

<210> SEQ ID NO 8
<211> LENGTH: 16
<212> TYPE: PRT
<213> ORGANISM: Artificial Sequence
<220> FEATURE:
<223> OTHER INFORMATION: derived from laminin

<400> SEQUENCE: 8

Ser Arg Asn Leu Ser Glu Ile Lys Leu Leu Ile Ser Gln Ala Arg Lys
1               5                   10                  15

<210> SEQ ID NO 9
<211> LENGTH: 29
<212> TYPE: PRT
<213> ORGANISM: Artificial Sequence
<220> FEATURE:
<223> OTHER INFORMATION: derived from laminin

<400> SEQUENCE: 9

Ser Arg Asn Leu Ser Glu Ile Lys Leu Leu Ile Ser Gln Ala Arg Lys
1               5                   10                  15

Gln Ala Ala Ser Ile Lys Val Ala Val Ser Ala Asp Arg
            20                  25

<210> SEQ ID NO 10
<211> LENGTH: 15
<212> TYPE: PRT
<213> ORGANISM: Artificial Sequence
<220> FEATURE:
<223> OTHER INFORMATION: derived from laminin

<400> SEQUENCE: 10

Lys Asp Phe Leu Ser Ile Glu Leu Phe Arg Gly Arg Val Lys Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: derived from laminin

<400> SEQUENCE: 11

Ser Ala Val Arg Lys Lys Leu Ser Val Glu Leu Ser Ile Arg Thr
1               5                   10                  15

<210> SEQ ID NO 12
<211> LENGTH: 25
<212> TYPE: PRT
<213> ORGANISM: Artificial Sequence
<220> FEATURE:
<223> OTHER INFORMATION: derived from laminin

<400> SEQUENCE: 12

Leu Gly Thr Arg Leu Arg Ala Gln Ser Arg Gln Arg Ser Arg Pro Gly
1               5                   10                  15

Arg Trp His Lys Val Ser Val Arg Trp
            20                  25
```

```
<210> SEQ ID NO 13
<211> LENGTH: 25
<212> TYPE: PRT
<213> ORGANISM: Artificial Sequence
<220> FEATURE:
<223> OTHER INFORMATION: derived from laminin

<400> SEQUENCE: 13

Pro Pro Pro Pro Leu Thr Ser Ala Ser Lys Ala Ile Gln Val Phe Leu
1               5                   10                  15

Leu Gly Gly Ser Arg Lys Arg Val Leu
            20                  25

<210> SEQ ID NO 14
<211> LENGTH: 22
<212> TYPE: PRT
<213> ORGANISM: Artificial Sequence
<220> FEATURE:
<223> OTHER INFORMATION: derived from laminin

<400> SEQUENCE: 14

Arg Leu Arg Ala Gln Ser Arg Gln Arg Ser Arg Pro Gly Arg Trp His
1               5                   10                  15

Lys Val Ser Val Arg Trp
            20

<210> SEQ ID NO 15
<211> LENGTH: 11
<212> TYPE: PRT
<213> ORGANISM: Artificial Sequence
<220> FEATURE:
<223> OTHER INFORMATION: derived from laminin

<400> SEQUENCE: 15

Pro Gly Arg Trp His Lys Val Ser Val Arg Trp
1               5                   10

<210> SEQ ID NO 16
<211> LENGTH: 18
<212> TYPE: PRT
<213> ORGANISM: Artificial Sequence
<220> FEATURE:
<223> OTHER INFORMATION: derived from laminin

<400> SEQUENCE: 16

Arg Ile Gln Asn Leu Leu Lys Ile Thr Asn Leu Arg Ile Lys Phe Val
1               5                   10                  15

Lys Leu

<210> SEQ ID NO 17
<211> LENGTH: 18
<212> TYPE: PRT
<213> ORGANISM: Artificial Sequence
<220> FEATURE:
<223> OTHER INFORMATION: derived from fibronectin

<400> SEQUENCE: 17

Gln Pro Pro Arg Ala Arg Ile Thr Gly Tyr Ile Ile Lys Tyr Glu Lys
1               5                   10                  15

Pro Gly

<210> SEQ ID NO 18
<211> LENGTH: 23
<212> TYPE: PRT
<213> ORGANISM: Artificial Sequence
<220> FEATURE:
```

<223> OTHER INFORMATION: derived from von willebrand factor

<400> SEQUENCE: 18

Tyr Ile Gly Leu Lys Asp Arg Lys Arg Pro Ser Glu Leu Arg Arg Ile
1               5                   10                  15

Ala Ser Gln Val Lys Tyr Ala
            20

<210> SEQ ID NO 19
<211> LENGTH: 20
<212> TYPE: PRT
<213> ORGANISM: Artificial Sequence
<220> FEATURE:
<223> OTHER INFORMATION: derived from protein C

<400> SEQUENCE: 19

Ser Glu Lys Thr Leu Arg Lys Trp Leu Lys Met Phe Lys Lys Arg Gln
1               5                   10                  15

Leu Glu Leu Tyr
            20

<210> SEQ ID NO 20
<211> LENGTH: 24
<212> TYPE: PRT
<213> ORGANISM: Artificial Sequence
<220> FEATURE:
<223> OTHER INFORMATION: synthetic sequence

<400> SEQUENCE: 20

Ala Arg Lys Lys Ala Ala Lys Ala Ala Arg Lys Lys Ala Ala Lys Ala
1               5                   10                  15

Ala Arg Lys Lys Ala Ala Lys Ala
            20

<210> SEQ ID NO 21
<211> LENGTH: 24
<212> TYPE: PRT
<213> ORGANISM: Artificial Sequence
<220> FEATURE:
<223> OTHER INFORMATION: synthetic sequence

<400> SEQUENCE: 21

Ala Lys Lys Ala Arg Ala Ala Lys Lys Ala Arg Ala Ala Lys Lys Ala
1               5                   10                  15

Arg Ala Ala Lys Lys Ala Arg Ala
            20

<210> SEQ ID NO 22
<211> LENGTH: 15
<212> TYPE: PRT
<213> ORGANISM: Artificial sequence
<220> FEATURE:
<223> OTHER INFORMATION: derived from vitronectin

<400> SEQUENCE: 22

Ala Lys Lys Gln Arg Phe Arg His Arg Asn Arg Lys Gly Tyr Arg
1               5                   10                  15

<210> SEQ ID NO 23
<211> LENGTH: 6
<212> TYPE: PRT
<213> ORGANISM: Artificial Sequence
<220> FEATURE:
<223> OTHER INFORMATION: derived from heparin-binding consensus sequence

<400> SEQUENCE: 23

```
Ala Lys Lys Ala Arg Ala
1               5

<210> SEQ ID NO 24
<211> LENGTH: 12
<212> TYPE: PRT
<213> ORGANISM: Artificial Sequence
<220> FEATURE:
<223> OTHER INFORMATION: derived from heparin-binding consensus sequence

<400> SEQUENCE: 24

Ala Lys Lys Ala Arg Ala Ala Lys Lys Ala Arg Ala
1               5                   10

<210> SEQ ID NO 25
<211> LENGTH: 8
<212> TYPE: PRT
<213> ORGANISM: Artificial Sequence
<220> FEATURE:
<223> OTHER INFORMATION: derived from heparin-binding consensus sequence

<400> SEQUENCE: 25

Ala Arg Lys Lys Ala Ala Lys Ala
1               5

<210> SEQ ID NO 26
<211> LENGTH: 16
<212> TYPE: PRT
<213> ORGANISM: Artificial Sequence
<220> FEATURE:
<223> OTHER INFORMATION: derived from heparin-binding consensus sequence

<400> SEQUENCE: 26

Ala Arg Lys Lys Ala Ala Lys Ala Ala Arg Lys Lys Ala Ala Lys Ala
1               5                   10                  15

<210> SEQ ID NO 27
<211> LENGTH: 24
<212> TYPE: PRT
<213> ORGANISM: Artificial Sequence
<220> FEATURE:
<223> OTHER INFORMATION: derived from synthetic K-H sequence

<400> SEQUENCE: 27

Ala His His Ala His Ala Ala His His Ala His Ala Ala His His Ala
1               5                   10                  15

His Ala Ala His His Ala His Ala
            20

<210> SEQ ID NO 28
<211> LENGTH: 24
<212> TYPE: PRT
<213> ORGANISM: Artificial Sequence
<220> FEATURE:
<223> OTHER INFORMATION: derived from synthetic K-H sequence

<400> SEQUENCE: 28

Ala His His His Ala Ala His Ala Ala His His His Ala Ala His Ala
1               5                   10                  15

Ala His His His Ala Ala His Ala
            20

<210> SEQ ID NO 29
<211> LENGTH: 18
<212> TYPE: PRT
<213> ORGANISM: Artificial Sequence
```

```
<220> FEATURE:
<223> OTHER INFORMATION: synthetic sequence

<400> SEQUENCE: 29

Gly His Arg Pro Leu Asp Lys Lys Arg Glu Glu Ala Pro Ser Leu Arg
1               5                   10                  15

Pro Ala

<210> SEQ ID NO 30
<211> LENGTH: 19
<212> TYPE: PRT
<213> ORGANISM: Artificial Sequence
<220> FEATURE:
<223> OTHER INFORMATION: synthetic sequence

<400> SEQUENCE: 30

Leu Val Thr Ser Lys Gly Asp Lys Glu Leu Arg Thr Gly Lys Glu Lys
1               5                   10                  15

Val Thr Ser

<210> SEQ ID NO 31
<211> LENGTH: 83
<212> TYPE: PRT
<213> ORGANISM: Artificial Sequence
<220> FEATURE:
<223> OTHER INFORMATION: derived from antimicrobial peptide

<400> SEQUENCE: 31

Lys His Asn Leu Gly His Gly His Lys His Glu Arg Asp Gln Gly His
1               5                   10                  15

Gly His Gln Arg Gly His Gly Leu Gly His Gly His Glu Gly Gln His
                20                  25                  30

Gly Leu Gly His Gly His Lys Phe Lys Leu Asp Asp Asp Leu Glu His
                35                  40                  45

Gln Gly Gly His Val Leu Asp His Gly His Lys His Lys His Gly His
        50                  55                  60

Gly His Gly Lys His Lys Asn Lys Gly Lys Lys Asn Gly Lys His Asn
65                  70                  75                  80

Gly Trp Lys

<210> SEQ ID NO 32
<211> LENGTH: 83
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 32

Lys His Asn Leu Gly His Gly His Lys His Glu Arg Asp Gln Gly His
1               5                   10                  15

Gly His Gln Arg Gly His Gly Leu Gly His Gly His Glu Gln Gln His
                20                  25                  30

Gly Leu Gly His Gly His Lys Phe Lys Leu Asp Asp Asp Leu Glu His
                35                  40                  45

Gln Gly Gly His Val Leu Asp His Gly His Lys His Lys His Gly His
        50                  55                  60

Gly His Gly Lys His Lys Asn Lys Gly Lys Lys Asn Gly Lys His Asn
65                  70                  75                  80

Gly Trp Lys
```

```
<210> SEQ ID NO 33
<211> LENGTH: 18
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 33

Ala Lys Lys Ala Arg Ala Ala Lys Lys Ala Arg Ala Ala Lys Lys Ala
1               5                   10                  15

Arg Ala

<210> SEQ ID NO 34
<211> LENGTH: 18
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 34

Gly His Arg Pro Leu Asp Lys Lys Arg Glu Glu Ala Pro Ser Leu Arg
1               5                   10                  15

Pro Ala

<210> SEQ ID NO 35
<211> LENGTH: 19
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 35

Leu Val Thr Ser Lys Gly Asp Lys Glu Leu Arg Thr Gly Lys Glu Lys
1               5                   10                  15

Val Thr Ser

<210> SEQ ID NO 36
<211> LENGTH: 15
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 36

Lys Asn Asn Gln Lys Ser Glu Pro Leu Ile Gly Arg Lys Lys Thr
1               5                   10                  15

<210> SEQ ID NO 37
<211> LENGTH: 6
<212> TYPE: PRT
<213> ORGANISM: Artificial Sequence
<220> FEATURE:
<223> OTHER INFORMATION: completely synthesized, derived from
      heparin-binding consensus sequence

<400> SEQUENCE: 37

Ala Lys Lys Ala Arg Ala
1               5

<210> SEQ ID NO 38
<211> LENGTH: 8
<212> TYPE: PRT
```

```
<213> ORGANISM: Artificial Sequence
<220> FEATURE:
<223> OTHER INFORMATION: completely synthesized, derived from
      heparin-binding consensus sequence

<400> SEQUENCE: 38

Ala Arg Lys Lys Ala Ala Lys Ala
1               5
```

ANTIMICROBIAL PEPTIDES WITH HEPARIN BINDING ACTIVITY

This is a Divisional of U.S. application Ser. No. 10/557,455, filed 1 Sep. 2006, and which application(s) are incorporated herein by reference.

FIELD OF INVENTION

The invention relates to antimicrobial peptides with heparin binding activity, being derived from endogenous mammalian proteins being substantially free from antimicrobial activity selected from the group consisting of laminin isoforms, complement factor C3, histidin rich glycoprotein and kininogen and having from 10 to 36 amino acid residues, wherein the antimicrobial peptides consists of at least four amino acid residues selected from the group consisting of K, R and H. The invention also relates to pharmaceutical compositions comprising said antimicrobial peptides and use of the antimicrobial peptides and/or antimicrobial/pharmaceutical compositions.

BACKGROUND OF INVENTION

Several infections are successfully combated by the immune system of a mammal such as a human being. However, in some instances, bacteria, fungi, or viruses are not always cleared, which may cause localised or generalised acute infections. This is a serious concern at perinatal-, burn-, or intensive care units, and in immunocompromised individuals. In other cases, a continuous bacterial persistence at epithelial surfaces may cause or aggravate chronic disease. In humans, this is exemplified by chronic skin ulcers, atopic dermatitis and other types of eczema, acne, or genitourinary infections.

Symptomatic infections may be treated by various medicaments. Some diseases may also be combated by for instance vaccines. However, vaccines are not always the best treatment option and for certain microorganisms no vaccine is available. When no protection is available treatment of the disease is pursued. Often the treatment is performed by the use of an antibiotic agent, which kills the microbe. However, during the last years several microbes have become resistant against antibiotic agents. Most likely, resistance problems will increase in the near future. Additionally, several individuals have developed allergy against the antibiotic agent, thereby reducing the possibility to effectively use certain antibiotic agents.

Epithelial surfaces of various organisms are continuously exposed to bacteria. During recent years the innate immune system, based on antibacterial peptides has been attributed important roles in the initial clearance of bacteria at biological boundaries susceptible to infection (Lehrer, R. I., and Ganz, T. (1999) Curr Opin Immunol 11: 23-27, Boman, H. G. (2000) Immunol. Rev. 173, 5-16). Antimicrobial peptides kill bacteria by permeating their membranes, and thus the lack of a specific molecular microbial target minimizes resistance development.

Several antimicrobial peptides and proteins, unrelated to the herein described peptides are known in the art.

U.S. Pat. No. 6,503,881 disclose cationic peptides being an indolicidin analogue to be used as an antimicrobial peptide. The cationic peptides being derived from different species, including animals and plants.

U.S. Pat. No. 5,912,230 disclose anti-fungal and anti-bacterial histatin-based peptides. The peptides being based on defined portions of the amino acid sequences of naturally occurring human histatins and methods for treatment of fungal and bacterial infections.

U.S. Pat. No. 5,717,064 disclose methylated lysine-rich lytic peptides. The lytic peptides being tryptic digestion resistant and non-natural. The lytic peptides are suitable for in vivo administration.

U.S. Pat. No. 5,646,014 disclose an antimicrobial peptide. The peptide was isolated from an antimicrobial fraction from silkworm hemolymph. The peptide exhibits excellent antimicrobial activity against several bacterial strains, such as Escherichia coli, Staphylococcus aureus and Bacillus cereus.

McCabe et al., J.Biol.Chem. Vol 277:27477-27488, 2002, describes an 37 kDa antimicrobial and chemotactic protein, azurocidin, containing the heparin binding consensus motifs XBBXBX and XBBBXXBX.

WO2004016653 disclose a peptide based on the 20-44 sequence of azurocidin. This peptide contains a loop structure linked by disulfide bridges.

U.S. Pat. No. 6,495,516 and related patents, disclose peptides based on the bactericidal 55 kDa protein bactericidal/permeability increasing protein (BPI). The peptides exerted antimicrobial effects as well as had heparin and LPS-neutralizing capacity.

WO 01/81578 discloses numerous sequences encoding G-coupled protein-receptor related polypeptides, which may be used for numerous diseases.

WO 00/27415 discloses peptides being suitable for inhibition of angiogenesis. The peptides being analogous of high molecular weight kininogen 5. The BLASTp search shows sequences, which are conserved or have similarities among different species such as kininogen without any indication of the function of such conserved regions or if they at all have any function as small peptides.

At present, over 700 different antimicrobial peptide sequences are known (www.bbcm.univ.trieste.it/~tossi/search.htm), including cecropins, defensins magainins and cathelicidins.

Even though there is a huge amount of antimicrobial peptides available today there is still an increased need of new improved antimicrobial peptides. Antimicrobial peptides which can be used to combat microbes and being resistant or tolerant against antibiotic agents and/or other antimicrobial agents. Additionally, there is a need for new antimicrobial peptides, which are non-allergenic when introduced into mammals such as human beings. Bacteria have encountered endogenously produced antimicrobial peptides during evolution without induction of significant resistance.

SUMMARY OF THE INVENTION

According to a first aspect, the invention relates to antimicrobial peptides with heparin binding activity, being derived from endogenous mammalian proteins being substantially free from antimicrobial activity selected from the group consisting of laminin isoforms, complement factor C3, histidin rich glycoprotein and kininogen and having from 10 to 36 amino acid residues, wherein the antimicrobial peptides consists of at least four amino acid residues, selected from the group consisting of K, R and H.

By providing such antimicrobial peptides, the risks for allergenic reactions to antimicrobial peptides may be reduced due to the fact that the peptides are derived from endogenous proteins and/or peptides. By using short peptides the stability of the peptide may be increased and the production costs reduced, as compared to longer peptides and proteins, whereby the invention may be economically advantageous.

The invention originates from the finding that peptides with heparin-binding motifs derived from non-antimicrobial endogenous proteins exhibit antimicrobial activities, as described by Andersson et al., *Eur J Biochem*, 2004, 271: 1219-1226, published after the priority date of the present application. The structural prerequisite for heparin-binding and the presence of heparin-binding motifs in various proteins, is generally well documented. This group of molecules includes various laminin isoforms, fibronectin, coagulation factors, growth factors, chemokines, histidine-rich glycoprotein, kininogen and many others (see Andersson et al., (2004) *Eur J Biochem* 271; 271:1219-26 and references therein), none of them being inherently antimicrobial.

The antimicrobial peptides and the corresponding antimicrobial/pharmaceutical compositions according to the invention provide peptides and compositions, which facilitate efficient prevention, reduction or elimination of microorganisms. Thereby the possibility to combat microorganisms, which are resistant or tolerant against the antibiotic agents, may be increased. Moreover, mammals, which are allergenic against commercially available antimicrobial agents, may be treated. By providing antimicrobial/pharmaceutical compositions, which are derived from endogenous proteins, the probability may be reduced or even eliminated that a mammal will develop allergy against these particular peptides. This makes the antimicrobial/pharmaceutical compositions useful for several applications in which the antimicrobial/pharmaceutical compositions contact a mammal either as a medicament or as an additive to prevent infections.

Additionally, the use of short peptides improves bioavailibility. Furthermore, the use of structurally distinct heparin-binding antimicrobial peptides with specific or preferable actions on Gram-negative and Gram-positive bacteria, or fungi, enables specific targeting of various microorganisms, thus minimising development of resistance and ecological problems. By supplementing peptides that already exist in the mammal, the risk of additional ecological pressure by novel antibiotics is further diminished. Finally, these formulations may also enhance the effect of endogenous antimicrobial peptides.

According to a second aspect, the invention relates to antimicrobial/pharmaceutical compositions comprising one or more antimicrobial peptides as defined above and an pharmaceutical acceptable buffer, diluent, carrier, adjuvant or excipient.

According to a third aspect, the invention relates to the use of the antimicrobial peptides and/or the antimicrobial/pharmaceutical compositions as defined herein after.

The inventive antimicrobial peptides increase the list of antimicrobial agents, which aid in the choice to prevent, reduce or eliminate microorganisms in all kind of applications including but not limited to those that invade or infect mammals such as the human being.

DETAILED DESCRIPTION OF THE INVENTION

Definitions

Figure 1:
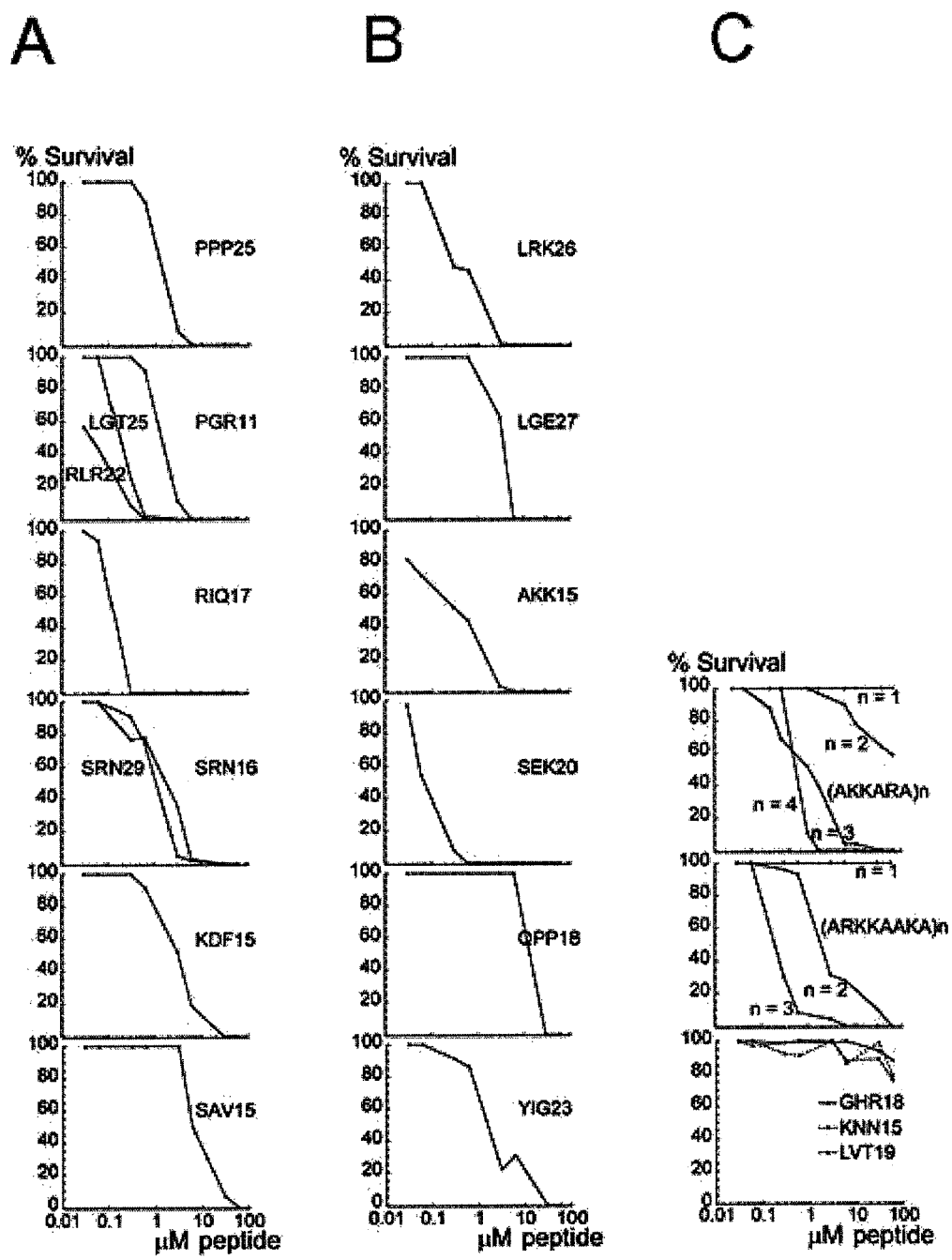
FIG. 1A-C are diagrams demonstrating the antibacterial effects of peptides on *Enterococcus faecalis*.

In the context of the present application and invention the following definitions apply:

The term "nucleotide sequence" is intended to mean a sequence of two or more nucleotides. The nucleotides may be of genomic DNA, cDNA, RNA, semi-synthetic or synthetic origin or a mixture thereof. The term includes single and double stranded forms of DNA or RNA.

The term "antimicrobial peptide" is intended to mean a peptide, which comprises from about 10 to about 36 amino acid residues, has anti-microbial and heparin binding activity and is derived from an endogenous mammalian which inherently has no antimicrobial effect. The "antimicrobial peptide" prevents, inhibits, reduces or destroys a microorganism. The antimicrobial activity can be determined by for example the method in EXAMPLE 2, 4 or 5.

The term "heparin binding affinity" is intended to mean a peptide, which binds to a heparin either directly or indirectly. The heparin binding activity can be determined by for example the method in EXAMPLE 7. The invented antimicrobial peptides, which exhibit affinity for heparin, also bind dermatan sulfate. Hence, heparin binding antimicrobial peptides, also interact with the endogenous glycosaminoglycan dermatan sulfate.

The term "amphipathic" is intended to mean the distribution of hydrophilic and hydrophobic amino acid residues along opposing faces of an a-helix structure, β-strand, linear, circular, or other secondary conformation, which result in one face of the molecule being predominantly charged and the other face being predominantly hydrophilic. The degree of amphipathicity of a peptide can be assessed by plotting the sequence of amino acid residues by various web-based algoritms, eg. those found on us.expasy.org/cgi-bin/protscale.pl. The distribution of hydrophobic residues can be visualized by helical wheel diagrams. Secondary structure prediction algoritms, such as GORIV can be found at www.expasy.com.

The term "cationic" is intended to mean a molecule, which has a net positive charge within the pH range of from about 4 to about 12.

The term "microorganism" is intended to mean any living microorganism. Examples of microorganisms are bacteria, fungus, virus, parasites and yeasts.

The term "antimicrobial agent" is intended to mean any agent, which prevent, inhibit or destroy life of microbes. Examples of antimicrobial agents can be found in The Sanford Guide to Antimicrobial Therapy (32nd edition, Antimicrobial Therapy, Inc, US).

In the present context, amino acid names and atom names are used as defined by the Protein DataBank (PNB) (www.p-db.org), which is based on the IUPAC nomenclature (IUPAC Nomenclature and Symbolism for Amino Acids and Peptides (residue names, atom names etc.), Eur J Biochem., 138, 9-37 (1984) together with their corrections in Eur J Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y), or derivatives thereof.

Description

Antimicrobial Peptide

The present invention relates to antimicrobial peptides with heparin binding activity, being derived from endogenous mammalian proteins being substantially free from antimicrobial activity and having from 10 to 36 amino acid residues, wherein the antimicrobial peptides consist of at least four amino acid residues selected from the group consisting of K, R and H. Two of the amino acid residues may be adjacent. A distance of ~20 Å between the B amino acid residues constitutes a prerequisite for heparin binding irrespective of peptide conformation as reported by Margalit et al., 1993 *J Biol Chem* 268, 19228-31. The use of short peptides increase bioavailibility of shorter peptides as compared to longer peptides or proteins, e.g., through an increased skin the penetration capacity as well as reduces the production and purification costs. The present antimicrobial peptides are complements to those antimicrobial peptides, which are commercially available today and increases the possibility to combat microorganisms, being tolerant and/or resistant against available antimicrobial agents. By deriving the new antimicrobial peptides from endogenous non-antimicrobial proteins it is possible to identify new peptides which are non-allergenic for the mammal from which the peptide has been based.

Furthermore, increased knowledge of peptide action and dependence of various salts and ionic environments enables design of specific compositions, which enhance and control peptide effects. Peptides scissored for actions on fungi will further be advantageous in targeting specific diseases, such as yeast infections on mucous membranes without significantly affecting bacterial ecology at these sites. The fact that antimicrobial peptides, act on bacterial membranes suggest that they may act synergistically together with antibiotics. Therefore, combination of antibiotics and peptides may have therapeutical advantages. Finally, there is also a need of antimicrobial agents, which are low cost and non-allergenic to be used in different kinds of products in which it is necessary to prevent growth of microorganisms.

Additionally, the use of structurally distinct heparin-binding short antimicrobial peptides with specific or preferable actions on Gram-negative and Gram-positive bacteria, or fungi enables specific targeting of various microorganisms, thus minimising resistance and ecological problems. By supplementing peptides that already occur in the organism, the risk of additional ecological pressure by novel antibiotics is further diminished. The introduction of specific formulations that enhance peptide effects localise and enhance exogenously supplied peptides which further minimises the risk of side effects of peptides, such as induction of resistance, outside the treated area. Finally, these formulations may also enhance the effect of endogenous antimicrobial peptides. If the antimicrobial peptides, are developed to be used to combat microorganisms in humans, the endogenous antimicrobial peptides are derived from human endogenous proteins. The same applies for other animals, such as horses, cows, pigs, or poultry. The antimicrobial peptides may be based on the structure of a peptide and/or protein present in plasma, blood, connective tissue and constituent cells and may be selected from the group consisting of heparin binding proteins; laminin isoforms, von Willebrand factor, vitronectin, protein C inhibitor, fibronectin, coagulation factors, growth factors, chemokines, histidin rich glycoprotein, kininogen, or complement factor C3.

The antimicrobial peptides of the invention have, a binding affinity (Kd) to heparin of about 10 nM to about 20 µM.

The peptides may have a size of 10, 11, 12, 13, 14, 15, 16, 17, 18, 19, 20, 21, 22, 23, 24, 25, 26, 27, 28, 29, 30, 31, 32, 33, 34, 35 or 36 amino acid residues. The length and sequence of the peptides is dependent on the origin of the antimicrobial peptides and which microorganism to combat, if the peptides are to be used to prevent, inhibit, reduce or destroy the microorganism and what kind of environment the microorganism is present in and what kind of environment the antimicrobial peptide will encounter after administration.

According to a first embodiment the invention relates to antimicrobial peptides being based on kininogen proteins or histidin rich glycoprotein, wherein at least 20% of the amino acid residues are H. The antimicrobial peptides may comprise more than 30, 40 or even 50% H, R and/or K amino acid residues. In specific examples 1,2,3,4,5 or 6 amino acid residues are H. For example the antimicrobial peptide may be selected from the group consisting of SEQ ID NO:1, 2, 3 and 4. These peptides are derived from heparin-binding domains of the non-antimicrobial proteins kininogen and histidine-rich glycoprotein, respectively and are rich in H residues.

According to another embodiment the invention relates to antimicrobial peptides being based on complement factor proteins. For example the antimicrobial peptide may be selected from the group consisting of SEQ ID NO: 5, 6 and 7. SEQ ID NO: 5, 6 and 7 peptides are derived from well-defined helical segments of the complement factor C3 molecule. As has been shown by Hugli and co-workers (Chazin et al., (1988) *Biochemistry* 27, 9139-48, Hugli, *Current topics in Microbiology and Immunology,* 1989, 153, 181-208) the helical regions of the C3-derived C3a molecule are defined by segments 19-28 (represented by SEQ ID NO: 5) and 47-70 (represented by SEQ ID NO: 6 and 7). The holoprotein C3 exerts no antimicrobial effects. The heparin binding and antimicrobial capacity of peptide segments derived from C3 has been disclosed recently (Andersson et al., *Eur J Biochem,* 2004, 271; 271:1219-1226).

According to a third embodiment the invention relates to antimicrobial peptides derived from the group of laminin proteins. For example the antimicrobial peptide may be selected from the group consisting of SEQ ID NO: 8, 9, 10, 11, 12, 13, 14, 15 and 16. Laminin α-chain LG-domains are composed of five (1-5) LG-modules that have been identified as binding sites for heparin and other cell-surface receptors (Timpl., et al., *Matrix Biol,* 2000, 19, 309-317). These modular proteins are synthesised during developmental processes such as wound healing and it has been described that proteolytic processing of LG-modules occur during these events. A previously undisclosed antimicrobial function of heparin-binding epitopes of LG-modules was described recently (Andersson et al., *Eur J Biochem,* 2004, 271; 271:1219-1226)

Even though the peptides are derived from endogenous proteins they may be produced as semisynthetic or even synthetic peptides as well as in microorganisms.

The antimicrobial peptides may be extended by one or more amino acid residues, such as 1-100 amino acid residues, 5-50 amino acid residues or 6, 7, 8, 9, 10, 11, 12, 13, 14, 15, 16, 17, 18, 19, 20, 21, 22, 23, 24, 25, 26, 27, 28, 29 and 30 amino acid residues. Such additional amino acids may duplicate a sequence contiguous to the sequence of the antimicrobial peptide derived from a non-antimicrobial protein. The number to be added depends on which microorganism to be combated in including, stability of the peptide, toxicity, the mammal to be treated or in which product the peptide should be in and which peptide structure the antimicrobial peptide is based upon. The number of amino acid residues to be added to the peptides depends also on the choice of production, e.g., expression vector and expression hosts and the choice of manufacturing the antimicrobial/pharmaceutical composition. The extension may be at the N- or C-terminal part or at both parts of the antimicrobial peptides as long as it does not disrupt the antimicrobial effect of the peptide. The antimicrobial peptides may also be a fusion protein, wherein the antimicrobial peptide is fused to another peptide.

Additionally the antimicrobial peptides may be operably linked to other known antimicrobial peptides or other substances, such other peptides, proteins, oligosaccharides, polysaccharides, other organic compounds, or inorganic substances. For example the antimicrobial peptides may be coupled to a substance which protect the antimicrobial peptides from being degraded within a mammal prior to the antimicrobial peptides has inhibited, prevented or destroyed the life of the microorganism.

Accordingly the antimicrobial peptides may be modified at the C-terminal part by amidation or esterification and at the N-terminal part by acylation, acetylation, PEGylation, alkylation and the like.

Alternatively, peptides derived from functional antimicrobial segments of non-antimicrobial holo-proteins may be modified by substitution of one to six amino acids.

Examples of microorganism that are inhibited, prevented or destroyed by the antimicrobial peptide are bacteria, both Gram positive and Gram-negative bacteria such as *Enterococcus faecalis, Eschericia coli, Pseudomonas aeruginosa, Proteus mirabilis, Streptococcus pneumoniae, Streptococcus pyogenes, Staphylococcus aureus*, viruse, parasites, fungus and yeast, such *Candida albicans* and *Candida parapsilosis*.

The antimicrobial peptides can be obtained from a naturally occurring source, such as from a human cell, a c-DNA, genomic clone, chemically synthesized or obtained by recombinant DNA techniques as expression products from cellular sources.

The antimicrobial peptides may be synthesized by standard chemical methods, including synthesis by automated procedure. In general, peptide analogues are synthesized based on the standard solid-phase Fmoc protection strategy with HATU (N-[DIMETHYLAMINO-1H-1.2.3.-TRIAZOLO[4,5-B]PYRIDIN-1-YLMETHYLELE]-N-METHYL-METHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

Peptides may alternatively be synthesized by recombinant production (see e.g., U.S. Pat. No. 5,593,866). A variety of host systems are suitable for production of the peptide analogues, including bacteria, such as *E. coli*, yeast, such as *Saccharomyces cerevisiae* or *pichia*, insects, such as Sf9, and mammalian cells, such as CHO or COS-7. There are many expression vectors available to be used for each of the hosts and the invention is not limited to any of them as long as the vector and host is able to produce the antimicrobial peptide.

Vectors and procedures for cloning and expression in E. Coli can be found in for example Sambrook et al. (Molecular Cloning.: A Laboratory Manual, Cold Spring Harbor Laboratory Press, Cold Spring Harbor, N.Y., 1987) and Ausubel et al. (Current Protocols in Molecular Biology, Greene Publishing Co., 1995).

Finally, the peptides may be purified from plasma, blood, various tissues or the like. The peptides may be endogenous, or generated after enzymatic or chemical digestion of the purified protein. For example, a heparin binding protein may be digested by trypsin and the resulting antibacterial peptides further isolated in larger scale.

A DNA sequence encoding the antimicrobial peptide is introduced into a suitable expression vector appropriate for the host. In preferred embodiments, the gene is cloned into a vector to create a fusion protein. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector. Preferably, the expression vector is a plasmid that contains an inducible or constitutive promoter to facilitate the efficient transcription of the inserted DNA sequence in the host.

The expression vector can be introduced into the host by conventional transformation techniques such as by calcium-mediated techniques, electroporation, or other methods well known to those skilled in the art.

The sequence encoding the antimicrobial peptide may be derived from a natural source such as a mammalian cell, an existing cDNA or genomic clone or synthesized. One method, which may be used, is amplification of the antimicrobial peptide by the aid of PCR using amplification primers which are derived from the 5' and 3' ends of the antimicrobial DNA template and typically incorporate restriction sites chosen with regard to the cloning site of the vector. If necessary, translational initiation and termination codons can be engineered into the primer sequences. The sequence encoding the antimicrobial peptide may be codon-optimized for facilitate expression in the particular host as long as the choice of the codons are made considering the final mammal to be treated. Thus, for example, if the antimicrobial peptide is expressed in bacteria, the codons are optimized for bacteria.

The expression vector should contain a promoter sequence, to facilitate expression of the introduced antimicrobial peptide. If necessary, regulatory sequences may also be included, such as one or more enhancers, ribosome binding site, transcription termination signal sequence, secretion signal sequence, origin of replication, selectable marker, and the like. The regulatory sequences are operably linked to each other to allow transcription and subsequent translation. If the antimicrobial peptide is o be expressed in bacteria, the regulatory sequences are those which are designed to e used within bacteria and such are well-known for a person skilled in the art. Suitable promoters, such as constitutive and inducible promoters, are widely available and includes promoters from T5, T7, T3, SP6 phages, and the trp, lpp, and lac operons.

If the vector containing the antimicrobial peptide is to be expressed within bacteria examples of origin are either those which give rise to a high copy number or those which give rise to a low copy, for example f1-ori and col E1 ori.

Preferably, the plasmids include at least one selectable marker that is functional in the host, which allows transformed cells to be identified and/or selectively grown. Suitable selectable marker genes for bacterial hosts include the ampicillin resistance gene, chloroamphenicol resistance gene, tetracycline resistance gene, kanamycin resistance gene and others known in the art.

Examples of plasmids for expression in bacteria include the pET expression vectors pET3a, pET 11a, pET 12a-c, and pET 15b (available from Novagen, Madison, Wis.). Low copy number vectors (e.g., pPD100) can be used for efficient overproduction of peptides deleterious to the E. coli host (Dersch et al., FEMS Microbiol. Lett. 123:19, 1994).

Examples of suitable hosts are bacteria, yeast, insects and mammal cells. However, often either bacteria such as E. coli is used.

The expressed antimicrobial peptide is isolated by conventional isolation techniques such as affinity, size exclusion, or ionic exchange chromatography, HPLC and the like. Different purification techniques can be found in A Biologist's Guide to Principles and Techniques of Practical Biochemistry (eds. Wilson and Golding, Edward Arnold, London, or in Current Protocols in Molecular Biology (John Wiley & Sons, Inc).

Antimicrobial/Pharmaceutical Composition

Additionally the invention relates to antimicrobial/pharmaceutical compositions comprising an antimicrobial peptide as described above and a pharmaceutical acceptable buffer, diluent, carrier, adjuvant or excipient. Additional compounds may be included in the compositions. These include, for example, chelating agents such as EDTA, EGTA or glutathione. The antimicrobial/pharmaceutical compositions may be prepared in a manner known in the art that is sufficiently storage stable and suitable for administration to humans and animals. The pharmaceutical compositions may be lyophilised e.g., through freeze drying, spray drying or spray cooling.

"Pharmaceutically acceptable" means a non-toxic material that does not interfere with the effectiveness of the biological activity of the active ingredients, i.e., the antimicrobial peptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO, TES, tricine.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycholate, citrate, borate, tartrate, and acetates of different acyl composition.

The excipient may be one or more of cabohydrates, polymers, lipids and minerals. Examples of carbohydrates include lactose, sucrose, mannitol, and cyclodextrines, which are added to the composition, e.g., for facilitating lyophilization. Examples of polymers are starch, cellulose ethers, cellulose carboxymethylcellulose, alginates,carageenans,hyaluronic acid, polyacrylic acid, polysulphonate, polyethylenglycol/ polyethylene oxide, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

The antimicrobial/pharmaceutical compositions may comprise one or more peptides, such as 1,2,3 or 4 different peptides in the antimicrobial/pharmaceutical compositions. By using a combination of different peptides the antimicrobial effect may be increased as well as decrease of the possibility that the microorganism to combat might be resistant and/or tolerant against the antimicrobial agent.

Histidin rich and/or kininogen based peptides, particularly as short peptides have limited antimicrobial activity. However if these peptides are in a composition comprising a salt and/or a pH from about 5.0 to about 7.0, the peptides become active, i.e., an enhanced effect is obtained by the addition of a salt and/or a choice of a specific pH range.

The peptide as a salt may be an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition. An antimicrobial H-rich peptides based on kininogen and histidine-rich glycoprotein may be used in defined solutions, such as gel, where the pH is defined and controlled (eg. pH 5.5-6.0) to enhance the effects of the added antimicrobial peptides. For example a gel, ointment or bandage, with a defined pH from about 5.0 to about 7.0, such as from about 5.5 to about 6.0 with or without an ionic environment will enhance, control, and localise the function of the antimicrobial peptides.

The antimicrobial/pharmaceutical compositions of the invention may also be in the form of a liposome in which the peptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Preparation of such liposomal formulations is can be found in for example U.S. Pat. No. 4,235,871.

The antimicrobial/pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP0213303.

Alternatively, the antimicrobial peptides may be dissolved in saline, water, polyethylene glycol, propylene glycol, ethanol or oils (such as safflower oil, corn oil, peanut oil, cottonseed oil or sesame oil), tragacanth gum, and/or various buffers. The pharmaceutical composition may also include ions and a defined pH for potentiation of action of antimicrobial peptides.

The antimicrobial/pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The antimicrobial/pharmaceutical compositions according to the invention may be administered locally or systemically. Routes of administration include topical, ocular, nasal, pulmonar, buccal, parenteral (intravenous, subcutaneous, and intramuscular), oral, parenteral, vaginal and rectal. Also administration from implants is possible. Suitable antimicrobial preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems characterized by long-range order but short-range disorder (examples include lamellar, hexagonal and cubic phases, either water- or oil continuous), or their dispersed counterparts, gels, ointments, dispersions, suspensions, creams, aerosols, droples or injectable solution in ampule form and also preparations with protracted release of active compounds, in whose preparation excipients, diluents, adjuvants or carriers are customarily used as described above. The pharmaceutical composition may also be provided in bandages or plasters or the like.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals The pharmaceutical compositions of the invention may be administered alone or in combination with other therapeutic agents, such as antibiotic or antiseptic agents such as antibacterial agents, anti-fuingicides, anti-viral agents, and anti-parasitic agents. Examples are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. These agents may be incorporated as part of the same pharmaceutical composition or may be administered separately.

The present invention concerns both humans and other mammal such as horses, dogs, cats, cows, pigs, camels, among others. Thus the methods are applicable to both human therapy and veterinary applications. The objects, suitable for such treatment may be identified by well-established hallmarks of an infection, such as fever, puls, culture of organisms, and the like. Infections that may be treated with the antimicrobial peptides include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions. Specific organisms in these classes are well known (see for example, Davis et al., Microbiology, 3.sup.rd edition, Harper & Row, 1980). Infections include, but are not limited to, chronic skin ulcers, infected acute wounds and burn wounds, infected skin eczema, impetigo, atopic dermatitis, acne, external otitis, vaginal infections, seborrhoic dermatitis, oral infections and parodontitis, candidal intertrigo, conjunctivitis and other eye infections, and pneumonia.

Accordingly the antimicrobial/pharmaceutical compositions may be used for prophylactic treatment of burn wounds, after surgery and after skin trauma. The pharmaceutical composition may also be included in solutions intended for storage and treatment of external materials in contact with the human body, such as contact lenses, orthopedic implants, and catheters.

Additionally, the antimicrobial/pharmaceutical compositions may be used for treatment of atopic dermatitis, impetigo, chronic skin ulcers, infected acute wound and burn wounds, acne, external otitis, fungal infections, pneumonia, seborrhoic dermatitis, candidal intertrigo, candidal vaginitis, oropharyngeal candidiasis, eye infections (bacterial conjunctivitis), and nasal infections (including MRSA carriage).

The antimicrobial/pharmaceutical compositions may also be used to in cleansing solutions, such as lens disinfectants and storage solutions or used to prevent bacterial infection in association with urinary catheter use or use of central venous catheters.

Additionally the antimicrobial compostions may be used for prevention of infection post-surgery in plasters, adhesives, sutures, or be incorporated in wound dressings.

The antimicrobial peptides may also be used in polymers, textiles or the like to create antibacterial surfaces or Cosmetics, and personal care products (soap, shampoos, tooth paste, anti-acne, suncreams, tampons, diapers, etc) may be supplemented with the antimicrobial/pharmaceutical compositions.

Method to Identify Antimicrobial Human Peptides and/or Proteins

The invention also relates to a method for the identification of one or more new antimicrobial peptide, which enables the possibility to provide mammals such as human beings with a new set of antimicrobial peptides having low allergenicity and being effective against the microorganism, which has invaded the mammal. By such a method new improved antimicrobial peptides will be available which provides a large collection of antimicrobial agents which reduce or even eliminates the problems of resistance and/or tolerance which are common today against the antibiotic agents available on the market.

The method comprising the steps of; providing the endogenous peptide and/or protein, providing heparin, mixing the endogenous peptide and/or protein with heparin creating a peptide and/or protein heparin complex, detecting the peptide and/or protein heparin complex and identifying the antimicrobial human endogenous peptide and/or protein. Additionally nickel such as nickelsepharose may be used instead of heparin. Heparin can be presented in solution, or connected to a matrix. In the latter case, this is suitable for separation purposes (h.p.l.c or f.p.l.c) or Biocore analysis. For separation purposes, Heparin-sepharose, or similar media may be used. Since antimicrobial peptides also interact with other glycosaminoglycans, it is possible to use these molecules, such as dermatan or heparan sulfate, for the purification of novel antimicrobial peptides. Heparin, heparan sulfate, and dermatan sulfate contains interspersed and spatially defined sulfo- or carboxyl-groups. In principal, any other polymeric compound of similar interactive capability as these glycosaminoglycans can be used for specific binding of antimicrobial peptides. Additionally, H-rich peptides may be purified on Nickel-sepharose or similar media, either alone or in combination with heparin-chromatography.

The following examples are intended to illustrate but not to limit the invention in any manner, shape, or form, either explicitly or implicitly.

EXAMPLES

Microorganisms

*Enterococcus faecalis* 2374, *Escherichia coli* 37.4, *Pseudomonas aeruginosa* 27.4, originally obtained from chronic venous ulcers, and the fungus *Candida albicans* BM 4435 obtained from an patient with atopic ezcema, were used in the experiments.

Example 1

Antimicrobial Peptides

The antimicrobial peptides shown in the sequence listing and Table 1 below were synthesized by Innovagen AB, Ideon, SE-22370, Lund, Sweden. The purity and molecular weight of these peptides was confirmed by mass spectral analysis (MALDI.TOF Voyager).

TABLE 1

| Origin | Peptide | Code |
| --- | --- | --- |
| C3a | LRKCCEDGMR ENPMRFSCQR RTRFIS | LRK26 (SEQ ID NO. 5) |
| C3a | LGEACKKVFL DCCNYITELR RQHARAS | LGE27 (SEQ ID NO. 6) |
| C3a | CNYITELRRQHARASHLGLAR | CNY21 (SEQ ID NO. 7) |
| Laminin-α1 | SRNLSEIKLLISQARK | SRN16 (SEQ ID NO. 8) |
| Laminin-α1 | SRNLSEIKLL ISQARKQAAS IKVAVSADR | SRN29 (SEQ ID NO. 9) |
| Laminin-α1 | KDFLSIELFR GRVKV | KDF15 (SEQ ID NO. 10) |
| Laminin-α1 | SAVRKKLSVE LSIRT | SAV15 (SEQ ID NO. 11) |
| Laminin-α5 | LGTRLRAQSR QRSRPGRWHK VSVRW | LGT25 (SEQ ID NO. 12) |
| Laminin-α5 | PPPPLTSASK AIQVFLLGGS RKRVL | PPP25 (SEQ ID NO. 13) |
| Laminin-α5 | RLRAQSRQRS RPGRWHKVSV RW | RLR22 (SEQ ID NO. 14) |
| Laminin-α1 | PGRWHKVSVR W | PGR11 (SEQ ID NO. 15) |
| Laminin-β1 | RIQNLLKITNLRIKFVKL | RIQ18 (SEQ ID NO. 16) |
| Fibronectin | QPPRARITGY IIKYEKPG | QPP18 (SEQ ID NO. 17) |
| Von Willebrand Factor | YIGLKDRKRP SELRRIASQV KYA | YIG23 (SEQ ID NO. 18) |
| Vitronectin | AKKQRFRHRN RKGYR | AKK15 (SEQ ID NO. 22) |
| Protein C inhibitor | SEKTLRKWLK MFKKRQLELY | SEK20 (SEQ ID NO. 19) |
| Histidine-rich glycoprotein | GHHPHGHHPH GHHPHGHHPH | GHH20 (SEQ ID NO. 4) |
| Kininogen | KHNLGHGHKH ERDQGHGHQR | KHN20 (SEQ ID NO. 3) |
| Kininogen | GGHVLDHKHGHGHGKHKNKG | GGH20 (SEQ ID NO. 2) |
| Kininogen | HKHGHGHGKH KNKGKKNGKH | HKH20 (SEQ ID NO. 1) |
| Synthetic sequence | AKKARAAKKA RAAKKARAAK KARA | AKK24 (SEQ ID NO. 21) |
| Synthetic sequence | AKKARAAKKA RAAKKARA | AKK18 (SEQ ID NO. 33) |
| Synthetic sequence | AKKARAAKKA RA | AKK12 (SEQ ID NO. 24) |

TABLE 1-continued

| Origin | Peptide | Code |
|---|---|---|
| Synthetic sequence | ARKKAAKAAR KKAAKAARKK AAKA | ARK24 (SEQ ID NO. 20) |
| Synthetic sequence | ARKKAAKAAR KKAAKA | ARK16 (SEQ ID NO. 26) |
| Synthetic K -> H sequence | AHHAHAAHHA HAAHHAHAAH HAHA | AHH24:1 (SEQ ID NO. 27) |
| Synthetic K -> H sequence | AHHHAAHAAH HHAAHAAHHH AAHA | AHH24:2 (SEQ ID NO. 28) |

Example 2

Antibacterial Effects of Arginine and Lysine-rich Peptides

FIG. 1 describes bactericidal effects of arginine and lysine-rich peptides (Sequence listing) on *Enterococcus faecalis*. Bacteria were grown to mid-logarithmic phase in Todd-Hewitt (TH) medium. Bacteria were washed and diluted in either 10 mM Tris, pH 7.4, containing 5 mM glucose Bacteria (50 µl; 2×10$^6$ cfu/ml) were incubated, at 37° C. for 2 hours, with the synthetic peptide at concentrations ranging from 0.03 to 60 µM. To quantify the bactericidal activity, serial dilutions of the incubation mixture were plated on TH agar, followed by incubation at 37° C. overnight and the number of colony-forming units was determined.

2×10$^6$ colony-forming units (CFU)×ml$^{-1}$ of *E. faecalis* (isolate 2374) were incubated in 50 µl with peptides at concentrations ranging from 0.03 to 60 µM. (A) Synthetic peptides derived from laminin. Effect of peptides from the LG-domain of the α5 chain (PPP25: SEQ ID NO:13, LGT25: SEQ ID NO:12, RLR22: SEQ ID NO:14, PGR11: SEQ ID NO:15) and α1 chain (SRN16: SEQ ID NO:8, SRN29:SEQ ID NO:9, KDF15:SEQ ID NO:10, SAV15:SEQ ID NO:11) are shown. One peptide (RIQ18:SEQ ID NO:16) is derived from the β1 chain. (B) Three peptides are derived from the complement factor C3 (LRK26:SEQ ID NO:5, LGE27:SEQ ID NO:6 and CNY21:SEQ ID NO:7), AKK15 from vitronectin, SEK20:SEQ ID NO: 19 from the protein C inhibitor, QPP18:SEQ ID NO:17 from fibronectin, and YIG23:SEQ ID NO:18 from the von Willebrand factor. (C) Antibacterial effects of heparin-binding consensus sequences (AKKARA)$_n$ (SEQ ID NO. 37) (n=1-4), and (ARKKAAKA)$_n$ (SEQ ID NO. 38) (n=1-3). The n=1 peptides exerted no antimicrobial effects. Peptides not interacting with heparin; GHRPLDKKREEAPSLRPA (SEQ ID NO. 34), LVTSKGDKELRTGKEKVTS, (SEQ ID NO. 35), and KNNQKSEPLIGRKKT (SEQ ID NO. 36) (Andersson et al., Eur J Biochem, 2004, 271; 271:1219-1226) were not antimicrobial.

Example 3

Radial Diffusion Assay Analysis of Antimicrobial Peptides (Table 2)

Radial diffusion assays (RDA) were performed essentially as described earlier (Andersson et al., *Eur J Biochem*, 2004, 271:1219-1226). Briefly, bacteria (*E. coli*) or fungi (*C. albicans*) were grown to mid-logarithmic phase in 10 ml of full-strength (3% w/v) trypticase soy broth (TSB) (Becton-Dickinson, Cockeysville, Md.). The microorganisms were washed once with 10 mM Tris, pH 7.4. 4×10$^6$ bacterial cfu or 1×10$^5$ fungal cfu was added to 5 ml of the underlay agarose gel, consisting of 0.03% (w/v) TSB, 1% (w/v) low-electroendosmosistype (Low-EEO) agarose (Sigma, St Louise Mo.) and a final concentration of 0.02% (v/v) Tween 20 (Sigma). The underlay was poured into a Ø 85 mm petri dish. After agarose solidified, 4 mm-diameter wells were punched and 6 µl of test sample was added to each well. Plates were incubated at 37° C. for 3 hours to allow diffusion of the peptides. The underlay gel was then covered with 5 ml of molten overlay (6% TSB and 1% Low-EEO agarose in dH$_2$O). Antimicrobial activity of a peptide is visualized as a clear zone around each well after 18-24 hours of incubation at 37° C. Synthetic peptides were tested in concentrations of 100 µM to determine the antibacterial effect relative the known peptide LL-37. To minimize variation between experiments, a LL-37 standard (100 µM) was included on each plate. The activities of the peptides are presented in radial diffusion units ((diameter of clear zone in millimeters—well diameter)×10). The results are shown in table 2 below.

TABLE 2

| Origin | Code | Radial diffusion units |
|---|---|---|
| hCAP-18 | LL-37 | 50 |
| C3a | LRK26 | 70 |
| C3a | LGE27 | 40 |
| C3a | CNY21 | 32 |
| Laminin-α1 | SRN16 | 77 |
| Laminin-α1 | SRN29 | 71 |
| Laminin-α1 | KDF15 | 65 |
| Laminin-α1 | SAV15 | 75 |
| Laminin-α5 | LGT25 | 85 |
| Laminin-α5 | PPP25 | 81 |
| Laminin-α5 | RLR22 | 92 |
| Laminin-α1 | PGR11 | 86 |
| Laminin-β1 | RIQ18 | 93 |
| Fibronectin | QPP18 | 59 |
| Von Willebrand Factor | YIG23 | 80 |
| Vitronectin | AKK15 | 101 |
| Protein C inhibitor | SEK20 | 92 |
| Synthetic sequence | AKK24 | 67 |
| Synthetic sequence | ARK24 | 74 |

Example 4

Figure 2:
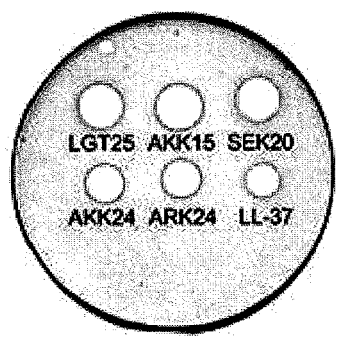
FIGS. 2A and B are petri dishes illustrating radial diffusion assays using a set of highly active peptides.
Figure 2:

Radial Diffusion Assay of of Peptides Against *E. coli* and *C. albicans* (FIG. 2).

FIG. 2 illustrates radial diffusion assays using a set of antimicrobial peptides. The assays were performed as above. Antimicrobial activity of a peptide was visualized as a clear zone around each well after 18-24 hours of incubation at 37° C. for *E. faecalis* bacteria (panel A) and 28° C. for *Candida albicans* (panel B).

Example 5

Antibacterial Effects of Histidine-rich Peptides

Figure 3:
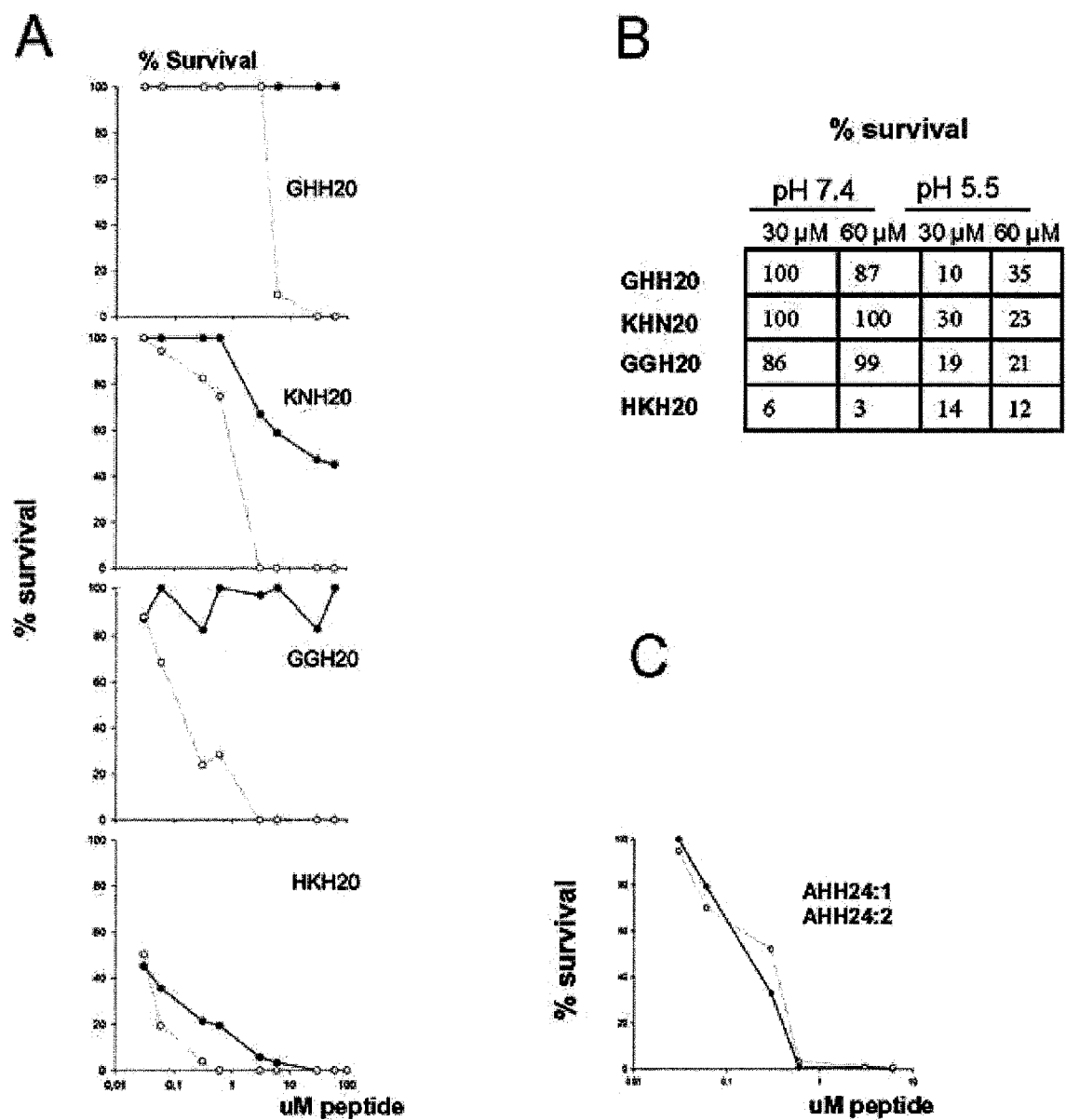
FIG. 3A-C are diagrams and a table describing antibacterial effects of histidine-rich peptides.

FIG. 3 describes bactericidal effects of histidine-rich peptides. *E. faecalis* bacteria were grown to mid-logarithmic phase in Todd-Hewitt (TH) medium. Bacteria were washed and diluted in either 10 mM Tris, pH 7.4, containing 5 mM glucose with or without 50 µM ZnCl or 10 mM MES-buffer, 5 mM glucose, pH 5.5. Bacteria (50 μl; 2×10$^6$ cfu/ml) were incubated, at 37° C. for 2 hours, with the synthetic peptide at concentrations ranging from 0.03 to 60 μM (Tris-buffer with or without zinc), or 30 and 60 uM (Tris and MES-buffer). To quantify the bactericidal activity, serial dilutions of the incubation mixture were plated on TH agar, followed by incubation at 37° C. overnight and the number of colony-forming units was determined. (A): effect of peptides from the heparin-binding domain of histidine-rich glycoprotein (GHH20: SEQ ID NO:4) and kininogen (KHN20: SEQ ID NO:3, GGH20: SEQ ID NO:2 and HKH20: SEQ ID NO:1) in the presence or absence of 50 uM ZnCl are shown. (B): Effects of peptides (30 and 60 uM) in 10 mM Tris, pH 7.4, containing 5 mM glucose or 10 mM MES-buffer, 5 mM glucose, pH 5.5. The numbers indicate % survival where 100% is control (without peptide). (C): Effects of peptides AHH24: 1 and AHH24:2 on *E. faecalis* in the presence of a fixed peptide/zinc molar ratio (1:100). Peptides without zinc exerted no antimicrobial activity.

Example 6

Analysis by Electron Microscopy of Peptide Effects

Figure 4:
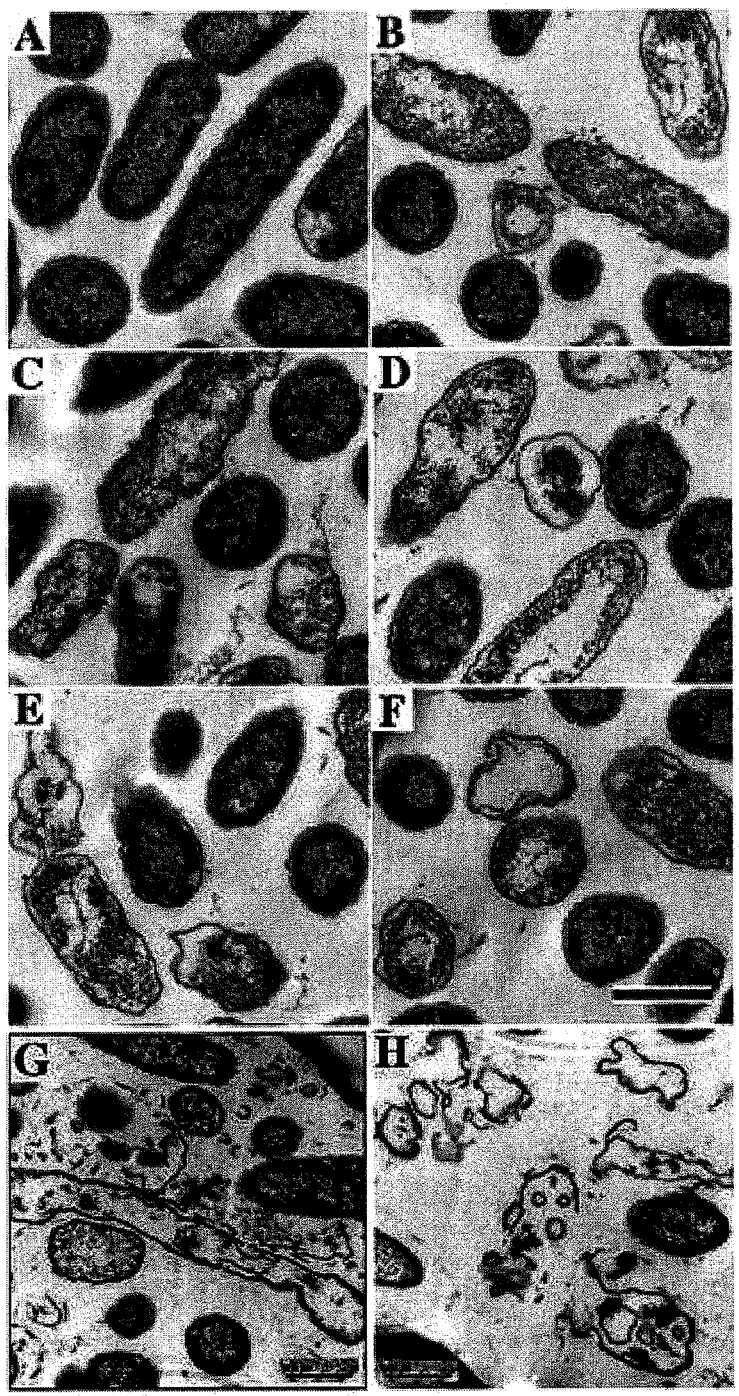
FIG. 4A-H are electron microscopy pictures showing the analysis of *Pseudomonas aeruginosa* subjected to antimicrobial peptides.

FIG. 4 shows electron microscopy analysis of *Pseudomonas aeruginosa* bacteria subjected to antimicrobial peptides. (A) Control. (B-H) Analysis of bacteria treated with peptides at ~50% of the required bactericidal concentration. HKH20 was also analysed at 200%. (B) LL-37, (C) ARK24, (D) SEK20, (E) AKK24, (F) LGT25 (G) HKH20, (H) HKH20 at 200% of bactericidal concentration. The bar represents 1 μm except for G and H (0.5 μm). Electron microscopy analysis of bacteria treated with peptides demonstrated clear differences in the morphology of treated bacteria in comparison with the control. The cathelicidin LL-37 caused local perturbations and breaks along *P. aeruginosa* bacterial cell membranes, and occasionally, intracellular material was found extracellularly and similar finding were obtained with the endogenous antimicrobial peptides herein disclosed.

Example 7

Figure 5:
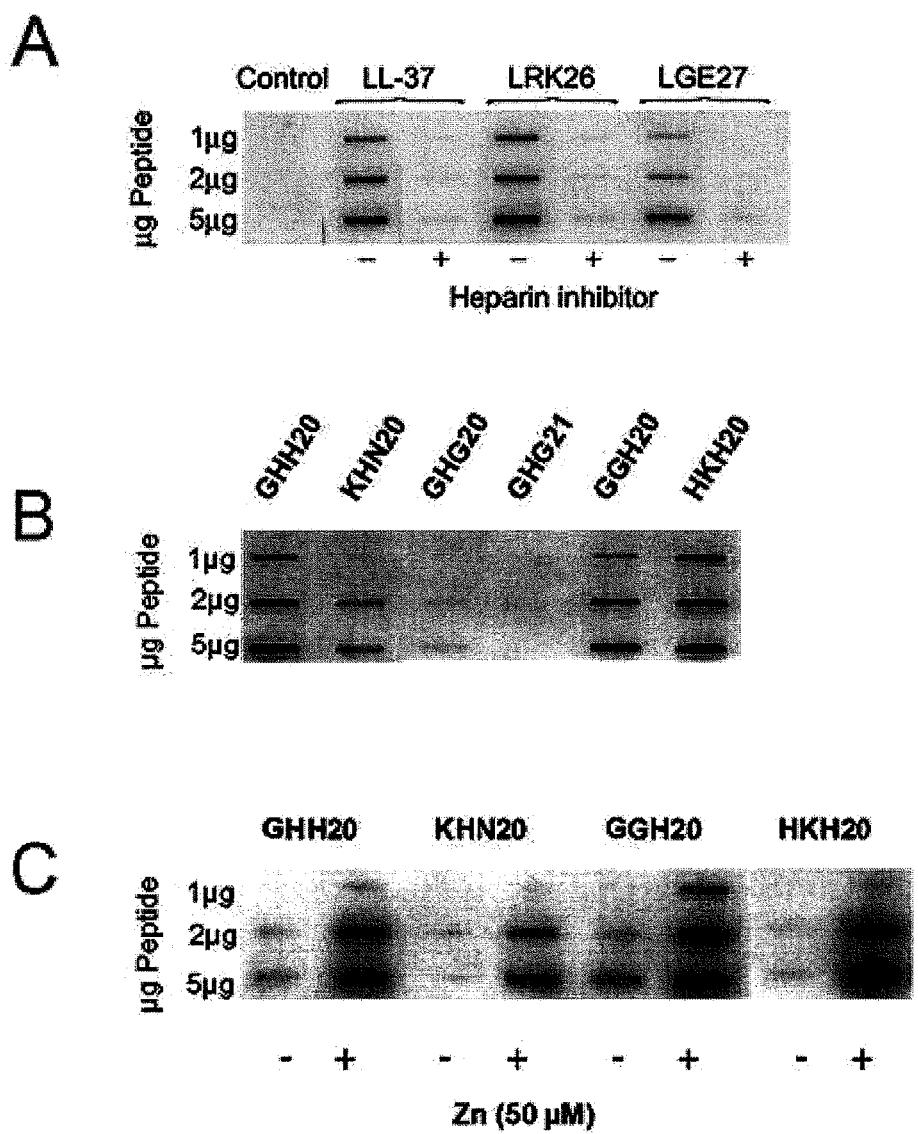
FIG. 5A-C are photograhs showing the heparin binding activity of peptides derived from complement C3, histidine-rich glycoprotein and kininogen.

Heparin Binding of Endogenous Antimicrobial Peptides (FIG. 5).

Peptides were tested for heparin binding activities. Peptides were applied on nitrocellulose membranes (Hybond, Amersham Biosciences). Membranes were blocked (PBS, pH 7.4, 0.25% Tween 20, 3% bovine serum albumin) for one hour and incubated with radiolabelled heparin for one hour in the same buffer. Histidine-rich peptides were tested for heparin-binding in the presence or absence of 50 μM ZnCl. The radioiodination of heparin was performed as described earlier (Andersson et al., *Eur J Biochem*, 2004, 271; 271:1219-1226). Unlabelled polysaccharides (2 mg/ml) were added for competition of binding. The membranes were washed (3×10 min in PBS, pH 7.4, 0.25% Tween 20). A Bas 2000 radioimaging system (Fuji) was used for visualization of radioactivity.

Unlabelled heparin (6 mg/ml) inhibited the binding of $^{125}$I-heparin to the C3-derived peptides LRK26 and LGE27 and LL-37 (upper part).

Example 8

Figure 6:
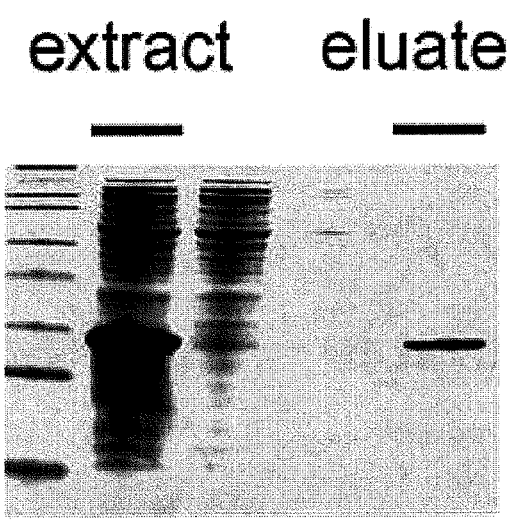
FIG. 6 is a photograph illustrating purification of histidine-containing antimicrobial fragment on nickel-sepharose.

Purification of Histidine-containing Antimicrobial Fragment on Nickel-sepharose (FIG. 6).

Domain D5 of human kininogen, which contains peptide epitopes KHN20, GGH20 and HKH20 was expressed in *Eschericia coli* strain (BL21DE3). Protein production was induced by addition of 1 mM isopropyl-thio-β-D-galactoside to exponentially growing bacteria. After 3 h incubation bacteria were harvested by centrifugation.

The pellet was resuspended in 50 mM phosphate, 300 mM NaCl, pH 8.0 (buffer A) and bacteria were lysed by repeated cycles of freeze-thawing. The lysate was then centrifuged at 29000 g for 30 min. The supernatant was mixed with 2 ml NiNTA-sepharose loaded with nickel and equilibrated with buffer A. The sepharose was loaded into a column and washed with 10 ml buffer A with 0.1% Triton X-100, 10 ml buffer A, 5 ml buffer a with 1 M NaCl, 5 ml buffer A, 10 ml 20% ethanol, 10 ml buffer A with 5 mM imidazol, and buffer A with 30 mM imidazole. Protein (arrow) was eluted in 500 mM imidazole. This domain exerts antibacterial effects against *E. coli* in radial diffusion assays.

The invention claimed is:

1. A method of treating an infection caused by a bacteria in or on a subject in need thereof, comprising:
administering to the subject a peptide selected from SEQ ID NO: 1, 2, or 3 to treat the infection.

2. The method of claim 1, wherein administering comprises administering a combination of peptides, said combination comprising a peptide of SEQ ID NO: 1.

3. The method of claim 1, comprising administering the peptide in the form of a composition comprising the peptide and a pharmaceutically acceptable buffer, diluent, carrier, adjuvant, or excipient.

4. The method of claim 3, wherein the composition comprises a salt.

5. The method of claim 4, wherein the salt is selected from the group consisting of monovalent sodium, potassium or divalent zinc, magnesium, copper and calcium.

6. The method of claim 5, wherein the cation in the salt is divalent zinc.

7. The method of claim 3, wherein the composition has a pH from about 5.0 to about 7.0.

8. The method of claim 3, wherein the composition further comprises 2 or 3 different polypeptides.

9. The method of claim 3, wherein the composition is in the form of granule, powder, tablet, coated tablet, capsule, suppository, syrup, emulsion, gel, ointment, suspension, cream, aerosol, droplet, injectable form, plaster, wound dressing, suture, or adhesive.

10. The method of claim 1, wherein the bacteria is selected from the group consisting of *Enterococcus faecalis, Escherichia coli, Pseudomonas aeruginosa, Proteus mirabilis, Streptococcus pneumoniae, Streptococcus pyogenes* and *Staphylococcus aureus*.

11. The method of claim 1, wherein the subject is a mammal.

12. The method of claim 2, comprising administering the combination of peptides in the form of a composition comprising the combination of peptides and a pharmaceutically acceptable buffer, diluent, carrier, adjuvant, or excipient.

13. The method of claim 12, wherein the composition comprises a salt.

14. The method of claim 13, wherein the salt is selected from the group consisting of monovalent sodium, potassium or divalent zinc, magnesium, copper and calcium.

15. The method of claim 14, wherein the cation in the salt is divalent zinc.

16. The method of claim 12, wherein the composition has a pH from about 5.0 to about 7.0.

17. The method of claim 12, wherein the composition further comprises 2 or 3 different polypeptides.

18. The method of claim 2, wherein the bacteria is selected from the group consisting of *Enterococcus faecalis, Escherichia coli, Pseudomonas aeruginosa, Proteus mirabilis, Streptococcus pneumoniae, Streptococcus pyogenes* and *Staphylococcus aureus*.

19. The method of claim 2, wherein the combination of peptides comprises one more peptides selected from SEQ ID NO:2 and SEQ ID NO:3.

* * * * *